United States Patent
Fan et al.

(10) Patent No.: US 9,734,987 B2
(45) Date of Patent: *Aug. 15, 2017

(54) METHOD AND SYSTEM FOR ADAPTIVELY SCANNING A SAMPLE DURING ELECTRON BEAM INSPECTION

(71) Applicant: KLA-Tencor Corporation, Milpitas, CA (US)

(72) Inventors: Gary Fan, Fremont, CA (US); David Chen, Portland, OR (US); Vivekanand Kini, Sunnyvale, CA (US); Hong Xiao, Pleasanton, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/018,104

(22) Filed: Feb. 8, 2016

(65) Prior Publication Data
US 2016/0155605 A1 Jun. 2, 2016

Related U.S. Application Data

(63) Continuation of application No. 14/260,053, filed on Apr. 23, 2014, now Pat. No. 9,257,260.
(Continued)

(51) Int. Cl.
*H01J 37/28* (2006.01)
*H01J 37/21* (2006.01)
(Continued)

(52) U.S. Cl.
CPC .......... *H01J 37/28* (2013.01); *G01N 23/2251* (2013.01); *H01J 37/04* (2013.01);
(Continued)

(58) Field of Classification Search
CPC .......... H01J 37/28; H01J 37/21; H01J 37/265; H01J 37/222; H01J 37/147; H01J 23/06
(Continued)

(56) References Cited

U.S. PATENT DOCUMENTS

| 4,918,358 A | 4/1990 | Aihara et al. |
| 5,408,098 A | 4/1995 | Wells |

(Continued)

FOREIGN PATENT DOCUMENTS

| EP | 0953203 A2 | 11/1999 |
| JP | 2007329081 A | 12/2007 |
| JP | 2012068051 A | 4/2012 |

OTHER PUBLICATIONS

PCT International Search Report for PCT/US2014/035572 dated Feb. 23, 2016, page.

*Primary Examiner* — David A Vanore
(74) *Attorney, Agent, or Firm* — Suiter Swantz pc llo

(57) ABSTRACT

A system for adaptive electron beam scanning may include an inspection sub-system configured to scan an electron beam across the surface of a sample. The inspection sub-system may include an electron beam source, a sample stage, a set of electron-optic elements, a detector assembly and a controller communicatively coupled to one or more portions of the inspection sub-system. The controller may assess one or more characteristics of one or more portions of an area of the sample for inspection and, responsive to the assessed one or more characteristics, adjust one or more scan parameters of the inspection sub-system.

36 Claims, 11 Drawing Sheets

Related U.S. Application Data

(60) Provisional application No. 61/816,720, filed on Apr. 27, 2013.

(51) Int. Cl.
    *G01N 23/225*     (2006.01)
    *H01J 37/147*     (2006.01)
    *H01J 37/04*     (2006.01)
    *H01J 37/26*     (2006.01)

(52) U.S. Cl.
    CPC .......... *H01J 37/147* (2013.01); *H01J 37/261* (2013.01); *H01J 2237/04* (2013.01); *H01J 2237/24592* (2013.01); *H01J 2237/2806* (2013.01); *H01J 2237/2817* (2013.01)

(58) Field of Classification Search
    USPC .... 250/310, 307, 311, 306, 396 R, 397, 398, 250/252.1, 370.08, 491.1
    See application file for complete search history.

(56) References Cited

U.S. PATENT DOCUMENTS

| | | | |
|---|---|---|---|
| 5,659,174 A | 8/1997 | Kaneoka et al. | |
| 5,869,833 A | 2/1999 | Richardson et al. | |
| 6,204,509 B1 | 3/2001 | Yahiro et al. | |
| 6,211,525 B1 | 4/2001 | Cowham | |
| 6,232,787 B1 | 5/2001 | Lo et al. | |
| 6,426,501 B1 | 7/2002 | Nakagawa | |
| 6,437,330 B1 | 8/2002 | Sugiyama | |
| 6,509,750 B1 | 1/2003 | Talbot et al. | |
| 6,552,490 B1 | 4/2003 | Cascone et al. | |
| 6,583,420 B1 | 6/2003 | Nelson et al. | |
| 6,852,983 B2 | 2/2005 | Matsuya et al. | |
| 7,078,690 B2 | 7/2006 | Simon et al. | |
| 7,135,677 B2 | 11/2006 | Kienzle et al. | |
| 7,291,841 B2 | 11/2007 | Nelson et al. | |
| 7,358,493 B2 | 4/2008 | Roberts et al. | |
| 7,361,896 B2 | 4/2008 | Honda et al. | |
| 7,368,732 B2 | 5/2008 | Van Der Veen | |
| 8,120,748 B2 | 2/2012 | Geh et al. | |
| 8,421,008 B2 | 4/2013 | Nozoe et al. | |
| 8,716,662 B1 | 5/2014 | MacDonald et al. | |
| 8,890,096 B2 | 11/2014 | Li et al. | |
| 9,257,260 B2 * | 2/2016 | Fan | H01J 37/147 |
| 2002/0008200 A1 | 1/2002 | Kuwahara | |
| 2003/0006372 A1 | 1/2003 | Morita et al. | |
| 2003/0094572 A1 | 5/2003 | Matsui et al. | |
| 2005/0253065 A1 | 11/2005 | Sengupta et al. | |
| 2006/0012791 A1 | 1/2006 | Reinhorn et al. | |
| 2006/0033987 A1 | 2/2006 | Stelzer et al. | |
| 2006/0278826 A1 | 12/2006 | Roberts et al. | |
| 2007/0280526 A1 | 12/2007 | Malik et al. | |
| 2008/0259297 A1 | 10/2008 | Kawakubo | |
| 2009/0272900 A1 | 11/2009 | Nir | |
| 2012/0145894 A1 | 6/2012 | Wu et al. | |
| 2012/0300056 A1 | 11/2012 | Ban et al. | |
| 2012/0305768 A1 | 12/2012 | Yamamoto et al. | |
| 2014/0319342 A1 | 10/2014 | Fan et al. | |
| 2015/0041643 A1 | 2/2015 | Li et al. | |

* cited by examiner

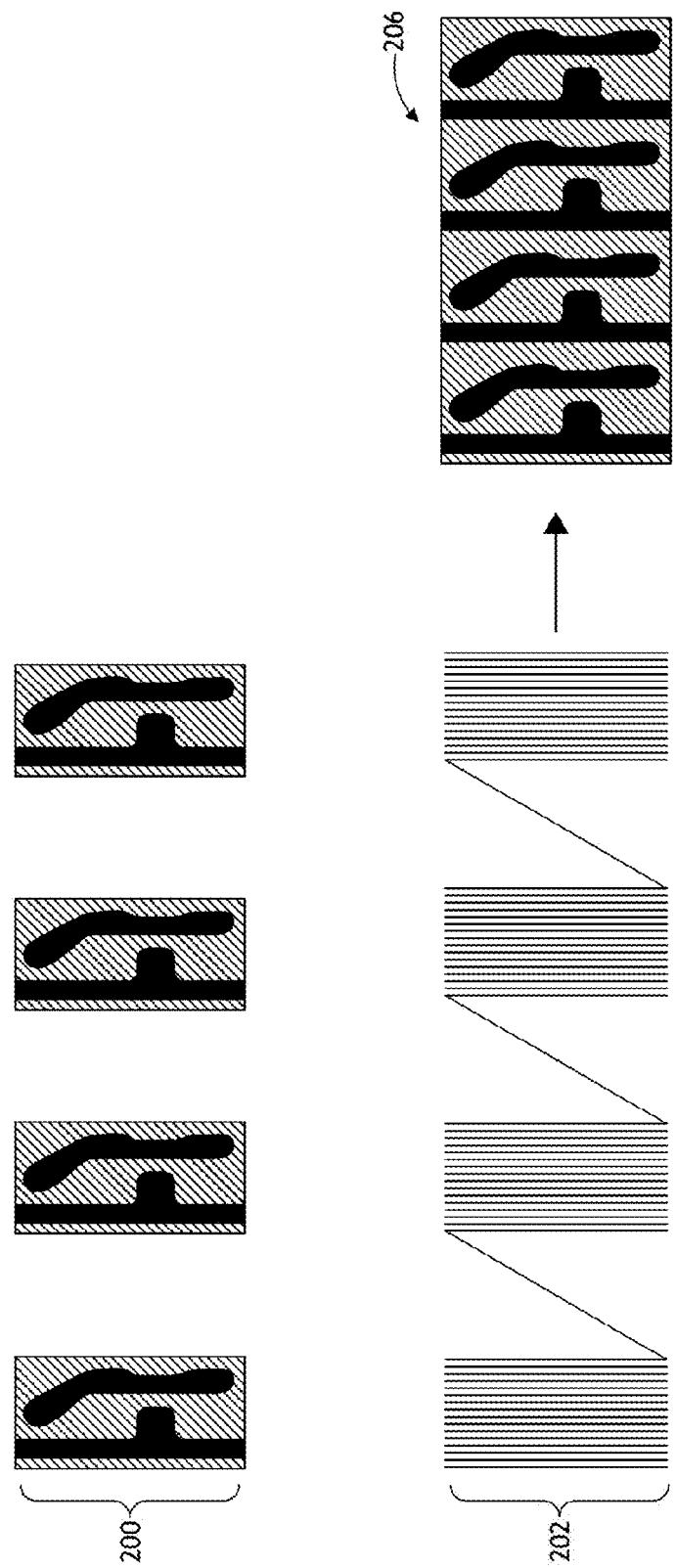

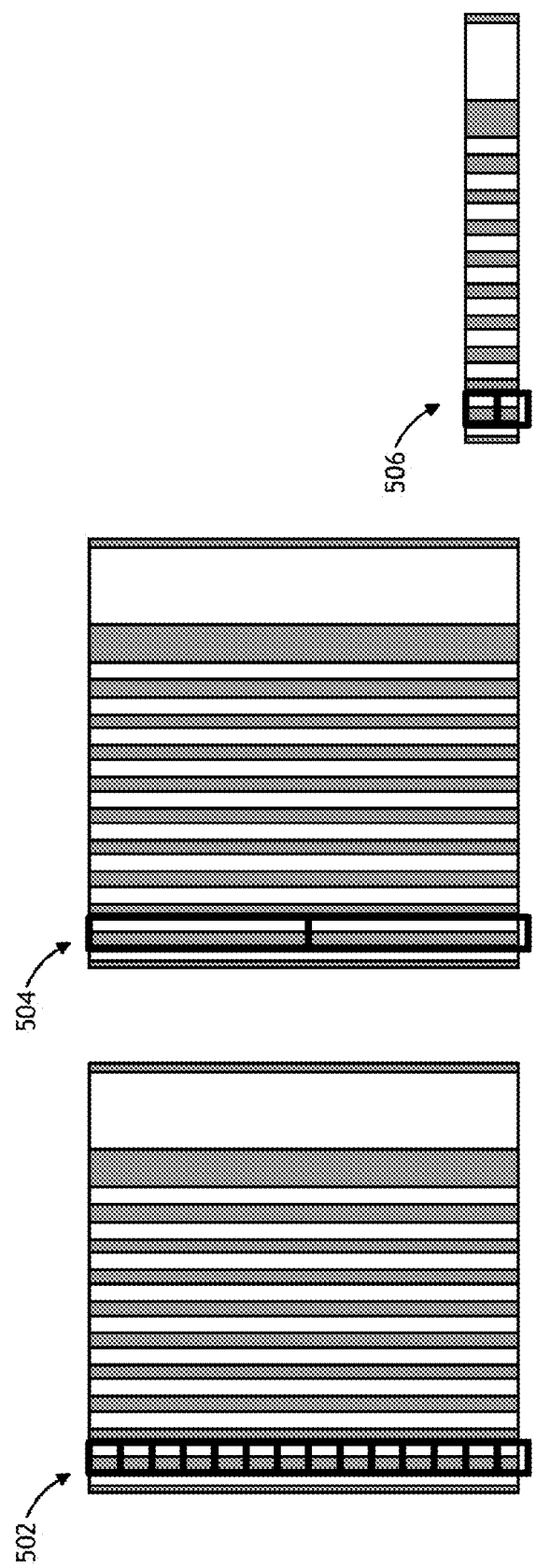

METHOD AND SYSTEM FOR ADAPTIVELY SCANNING A SAMPLE DURING ELECTRON BEAM INSPECTION

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

The present application constitutes a continuation application of United States Non-Provisional Patent Application entitled METHODS AND SYSTEM FOR ADAPTIVELY SCANNING A SAMPLE DURING ELECTRON BEAM INSPECTION, naming GARY FAN, DAVID CHEN, VIVEKANAND KINI AND HONG XIAO as inventors, filed Apr. 23, 2014, Application Ser. No. 14/260,053, which constitutes a non-provisional patent application of United States Provisional Patent Application entitled METHODS OF IMPROVING THROUGHOUT AND SENSITIVITY OF E-BEAM INSPECTION SYSTEM, naming Gary Fan, David Chen, Vivekanand Kini and Hong Xiao as inventors, filed Apr. 27, 2013, Application Ser. No. 61/816,720. The applications listed above are incorporated herein by reference in their entirety.

TECHNICAL FIELD

The present invention generally relates to electron beam sample inspection, and, in particular, to adaptively scanning a sample during electron beam inspection.

SUMMARY

A system for adaptively scanning a sample during electron beam inspection is disclosed. In one illustrative embodiment, the system may include, but is not limited to, an inspection sub-system configured to scan an electron beam across the surface of the sample, the inspection sub-system including: an electron beam source configured to generate an electron beam, a sample stage configured to secure the sample; and a set of electron-optic elements configured to direct the electron beam onto the sample; a detector assembly including at least an electron collector, the detector configured to detect electrons from the surface of the sample; a controller communicatively coupled to one or more portions of the inspection sub-system, the controller including one or more processors configured to execute program instructions configured to cause the one or more processors to: assess one or more characteristics of one or more portions of an area for inspection; and responsive to the assessed one or more characteristics, adjust one or more scan parameters of the inspection sub-system.

A method for adaptively scanning a sample during electron beam inspection is disclosed. In one illustrative embodiment, the method may include, but is not limited to, scanning an electron beam across a surface of the sample; assessing one or more characteristics of one or more portions of an area for inspection; and performing an inline adjustment of one or more electron beam scanning parameters associated with the scanning of the electron beam across the surface of the sample based on the one or more assessed characteristics of the of one or more portions of the area for inspection.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which:

FIGS. 2A-2E are conceptual views of a series of adaptive electron beam scanning scenarios, in accordance with embodiments of the present invention.

FIGS. 5A-5C are conceptual views of a series of adaptive electron beam scanning scenarios involving the elongation of pixels along a selected direction, in accordance with embodiments of the present invention.

DETAILED DESCRIPTION OF THE INVENTION

Reference will now be made in detail to the subject matter disclosed, which is illustrated in the accompanying drawings.

Referring generally to FIGS. 1 through 6, a method and system for adaptively scanning a sample during electron beam inspection is described in accordance with the present disclosure. Embodiments of the present disclosure are directed to the adaptive scanning of a sample, such as a semiconductor wafer, during electron beam inspection. In some embodiments, one or more scan parameters associated with a given scanning scenario may be adjusted, inline, in an effort to improve one or more scanning features. In other embodiments, the inline adjustment of scan parameters may be carried out in response to one or more assessed characteristics of an area or sub-area of a sample to be inspected. These characteristics may include, but are not limited to, pattern density, pattern complexity, dominant structural orientation, defect(s) size, defect density, defect depth and defect type. In additional embodiments, the assessment of the characteristics may be carried out during inspection recipe setup, during a setup run prior to inspection or during an inspection runtime. The inline adjusted of one or more scan parameters may lead to improved inspection speed, improved inspection sensitivity, detection of multiple types of defects in a single inspection, reduced false rate, reduced nuisance rate, reduced electron dose on sample and the like.

Figure 1:
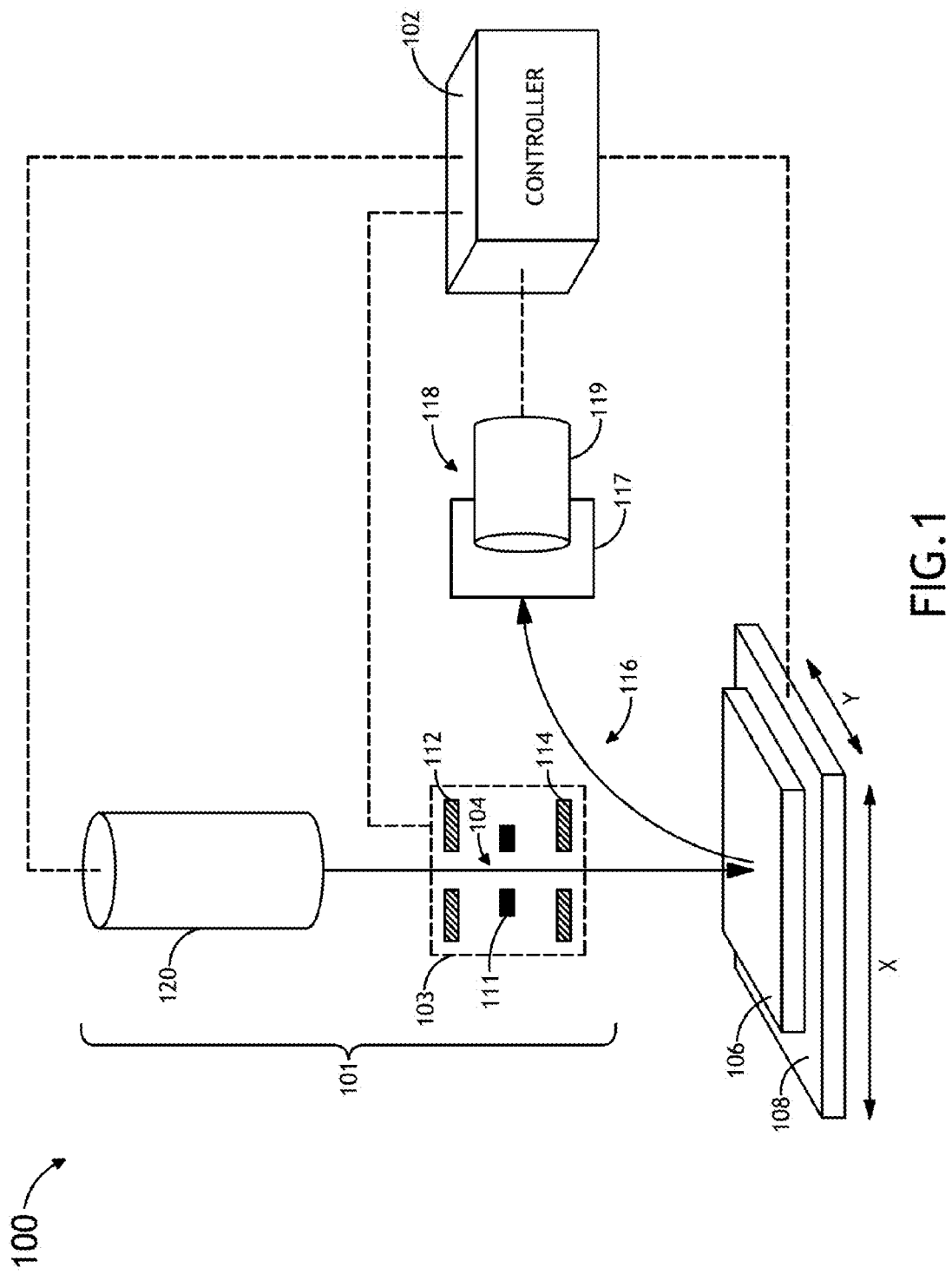
FIG. 1 is a high level schematic illustration of a system for adaptively scanning a sample during electron beam inspection, in accordance with one embodiment of the present invention.

FIG. 1 illustrates a system 100 for adaptively scanning a sample during electron beam inspection, in accordance with one embodiment of the present invention. In one embodiment, the system 100 includes an inspection sub-system 101. In one embodiment, the inspection sub-system 101 is an electron beam based inspection sub-system 101 suitable for scanning an electron beam 104 across a selected region of a sample 106. In one embodiment, sample 106 includes, but is not limited to, a wafer (e.g., semiconductor wafer). In another embodiment, one or more portions of the inspection sub-system are selectably controllable in order to adaptively scan the sample 106 with an electron beam 104. In one embodiment, one or more portions, or components, of the inspection sub-system 101 may be selectably controllable, independently or in conjunction with one or more other components, to vary, inline, one or more scan parameters of the inspection sub-system 101 based on one or more characteristics of an area (or sub-areas) of the sample 106 for inspection. For example, the one or more adjustable scan parameters of the inspection sub-system 101 include, but are not limited to, one or more electron source parameters (e.g., beam current). By way of another example, the one or more adjustable scan parameters of the inspection sub-system 101 include, but are not limited to, one or more stage parameters (e.g., stage scanning speed or sample bias voltage). By way of another example, the one or more adjustable scan parameters of the inspection sub-system 101 include, but are not limited to, one or more electron-optic parameters, such as one or more electron-optic focus parameters or one or more electron beam scanning parameters (e.g., scanning pattern, scan-line density, scan-line spacing, electron beam scanning speed, scanning range or field of scanning). By way of another example, the one or more adjustable scan parameters of the inspection sub-system 101 include, but are not limited to, one or more image forming parameters (e.g., extraction voltage, extraction field strength for secondary electrons or electron landing energy). By way of another example, the one or more adjustable scan parameters of the inspection sub-system 101 include, but are not limited to, one or more digitization parameters (e.g., digitization or pixel data rate).

In another embodiment, the one or more characteristics of the area (or sub-area) of the sample with which the scanning parameter adjustment may be based includes the complexity of one or more patterns of the sample. For example, a complexity marker (e.g., variation of line scan density) may be implemented to rank the complexity of various patterns of an area for inspection, as described further herein. In another embodiment, the one or more characteristics of the area (or sub-area) include one or more structural characteristics of one or more patterns of the sample. In another embodiment, the one or more characteristics of the area (or sub-area) include one or more defect characteristics of the sample. For example, the one or more characteristics of the area (or sub-area) may include, but are not limited to, a defect density within one or more portions of the area for inspection. By way of another example, the one or more characteristics of the area (or sub-area) may include, but are not limited to, a defect size within one or more portions of the area for inspection. By way of another example, the one or more characteristics of the area (or sub-area) may include, but are not limited to, a defect type within the one or more portions of the area for inspection.

It is noted herein that the inspection sub-system 101 may operate in any scanning mode known in the art. For example, the inspection sub-system 101 may operate in a swathing mode when scanning an electron beam 104 across the surface of the sample 106. In this regard, the inspection sub-system 101 may scan an electron beam 104 across the sample 106, while the sample is moving, with the direction of scanning being nominally perpendicular to the direction of the sample motion. By way of another example, the inspection sub-system 101 may operate in a step-and-scan mode when scanning an electron beam 104 across the surface of the sample 106. In this regard, the inspection sub-system 101 may scan an electron beam 104 across the sample 106, which is nominally stationary when the beam 104 is being scanned.

In another embodiment, the system 100 includes a controller 102. In one embodiment, the controller 102 is communicatively coupled to one or more portions of the inspection sub-system 101. In one embodiment, the controller 102 is configured to assess one or more characteristics of one or more portions of an area for inspection. In one embodiment, the controller 102 may assess the one or more characteristics during inspection recipe setup, during a setup run prior to inspection or during an inspection runtime. In another embodiment, the controller 102 is configured to, in response to the assessed one or more characteristics, adjust one or more scan parameters of the inspection sub-system.

In one embodiment, the controller 102 may assess, or measure, one or more characteristics of an area (or sub-area) of the sample 106. In one embodiment, the controller 102 may assess the complexity, or a complexity marker or metric, of one or more patterns of the sample 106. In another embodiment, the controller 102 may assess one or more structural characteristics of one or more patterns of the sample 106. In another embodiment, the controller 102 may assess one or more defect characteristics of the sample 106. For example, controller 102 may assess, or measure, a defect density within one or more portions of the area for inspection. By way of another example, controller 102 may assess, or measure, a defect size within the one or more portions of the area for inspection. By way of another example, controller 102 may assess, or measure, a defect type within the one or more portions of the area for inspection In one embodiment, the controller 102 may adjust one or more electron source parameters (e.g., beam current). In another embodiment, the controller 102 may adjust one or more stage parameters (e.g., stage scanning speed or sample bias voltage). In another embodiment, the controller 102 may adjust one or more electron-optic parameters, such as one or more electron-optic focus parameters (e.g., focus) or one or more electron beam scanning parameters (e.g., scanning pattern, scan-line density, scan-line spacing, electron beam scanning speed, scanning range or field of scanning). In another embodiment, the controller 102 may adjust one or more image forming parameters (e.g., extraction voltage, extraction field strength for secondary electrons or electron landing energy). For example, the controller 102 may vary the electron beam landing energy from one sub-area to another in order to enhance the defect signal in each sub-area or to make the defect-of-interest in each sub-area more readily detectable. By way of another example, the controller 102 may vary the extraction field or voltage controlling imaging electrons from one sub-area to another in order to enhance the defect signal in each sub-area or to make the defect-of-interest in each sub-area more readily detectable.

In another embodiment, the controller 102 may adjust one or more digitization parameters (e.g., digitization or pixel data rate).

In one embodiment, the inspection sub-system 101 includes an electron beam source 120 for generating one or more electron beams 104. The electron beam source 120 may include any electron source known in the art. For example, the electron beam source 120 may include, but is not limited to, one or more electron guns. In one embodiment, the controller 102 is communicatively coupled to the electron source 120. In another embodiment, the controller 102 may adjust one or more electron source parameters via a control signal to the electron source 120. In another embodiment, the controller 102 may adjust one or more one or more electron source parameters in response to the one or more assessed characteristics of the area of the sample for inspection. For example, the controller 102 may vary the beam current for the electron beam 104 emitted by source 120 via a control signal transmitted to control circuitry of the electron beam source 120.

In another embodiment, the sample 106 is disposed on a sample stage 108 suitable for securing the sample 106 during scanning. In another embodiment, the sample stage 108 is an actuatable stage. For example, the sample stage 108 may include, but is not limited to, one or more translational stages suitable for selectably translating the sample 106 along one or more linear directions (e.g., x-direction, y-direction and/or z-direction). By way of another example, the sample stage 108 may include, but is not limited to, one or more rotational stages suitable for selectably rotating the sample 106 along a rotational direction. By way of another example, the sample stage 108 may include, but is not limited to, a rotational stage and a translational stage suitable for selectably translating the sample along a linear direction and/or rotating the sample 106 along a rotational direction.

In one embodiment, the controller 102 is communicatively coupled to the sample stage 108. In another embodiment, the controller 102 may adjust one or more stage parameters via a control signal transmitted to the sample stage 108. In another embodiment, the controller 102 may adjust one or more one or more stage parameters in response to the one or more assessed characteristics of the area of the sample for inspection. For example, the controller 102 may vary the sample scanning speed via a control signal transmitted to control circuitry of the sample stage 108. For instance, the controller 102 may vary the speed with which sample 106 is linearly translated (e.g., x-direction or y-direction) relative to the electron beam 104.

In another embodiment, the inspection sub-system 101 includes a set of electron-optic elements 103. The set of electron-optics may include any electron-optic elements known in the art suitable for focusing and/or directing the electron beam 104 onto a selected portion of the sample 106. In one embodiment, the set of electron-optics elements includes one or more electron-optic lenses. For example, the electron-optic lenses may include, but are not limited to, one or more condenser lenses 112 for collecting electrons from the electron beam source. By way of another example, the electron-optic lenses may include, but are not limited to, one or more objective lenses 114 for focusing the electron beam onto a selected region of the sample 106.

In another embodiment, the set of electron-optics elements includes one or more electron beam scanning elements. For example, the one or more electron beam scanning elements 111 may include, but are not limited to, one or more scanning coils or deflectors suitable for controlling a position of the beam relative to the surface of the sample 106. In this regard, the one or more scanning elements 111 may be utilized to scan the electron beam 104 across the sample 106 in a selected pattern.

In one embodiment, the controller 102 is communicatively coupled to the set of electron-optic elements 103. In another embodiment, the controller 102 may adjust one or more electron-optic parameters via a control signal transmitted to one or more of the set of electron-optic elements 103. In another embodiment, the controller 102 may adjust one or more electron-optic parameters in response to the one or more assessed characteristics of the area of the sample for inspection.

In one embodiment, the controller 102 is communicatively coupled to the one or more electron-optic lenses 112, 114 of the set of electron-optic elements 103 and is configured to control one or more electron-optic focus parameters (e.g., electron-optic focus). For example, the controller 102 may vary the focus of electron beam 104 via a control signal transmitted to electron-optic lenses 112 or 114. In another embodiment, the controller 102 is communicatively coupled to the one or more electron beam scanning elements 111 of the set of electron-optic elements 103 and is configured to control one or more electron beam scanning parameters. For example, the controller 102 may vary the electron beam scan speed, scan range, field of scanning, scan-line density or line spacing via one or more control signals transmitted to the electron beam scanning elements 111.

In another embodiment, the inspection sub-system includes a detector assembly 118. In another embodiment, the controller 102 may adjust one or more digitization parameters via a control signal transmitted to one or more portions of the detector assembly 118. In another embodiment, the controller 102 may adjust one or more digitization parameters in response to the one or more assessed characteristics of the area of the sample for inspection.

In one embodiment, the detector assembly 118 includes an electron collector 117 (e.g., secondary electron collector). In another embodiment, the detector assembly 118 includes a detector 119 (e.g., scintillating element and PMT detector 119) for detecting electrons from the sample surface (e.g., secondary electrons). In another embodiment, the controller 102 is communicatively coupled to the electron collector 117. In one embodiment, the controller 102 may adjust one or more image forming parameters via a control signal transmitted to the collector 117. In one embodiment, the controller 102 may adjust the extraction voltage or the extraction field strength for the secondary electrons. For example, the controller 102 may vary the electron beam landing energy from one sub-area to another in order to enhance the defect signal in each sub-area or to make the defect-of-interest in each sub-area more readily detectable. In another embodiment, the controller 102 may adjust the electron landing energy on the sample 106. For example, the controller 102 may vary the extraction field or voltage controlling imaging electrons from one sub-area to another in order to enhance the defect signal in each sub-area or to make the defect-of-interest in each sub-area more readily detectable. In another embodiment, the controller 102 may adjust the sample bias voltage.

While the foregoing description focused on the detector assembly 118 in the context of the collection of secondary electrons, this should not be interpreted as a limitation on the present invention. It is recognized herein that the detector assembly 118 may include any device or combination of devices known in the art for characterizing a sample surface or bulk with an electron beam 104. For example, the detector assembly 118 may include any particle detector known in the art configured to collect backscattered electrons, Auger electrons, transmitted electrons or photons (e.g., x-rays emitted by surface in response to incident electrons).

In another embodiment, the controller 102 is communicatively coupled to the detector 119 of the detector assembly 118. In one embodiment, the controller 102 may adjust one or more digitization parameters via a control signal transmitted to the detector 119. For example, the controller 102 may adjust the digitization or pixel data rate of the detector 119 via a control signal transmitted to the detector 119.

In another embodiment, the detector of the detector assembly 118 includes a light detector. For example, the anode of a PMT detector of the detector 119 may consist of a phosphor anode, which is energized by the cascaded electrons of the PMT detector absorbed by the anode and subsequently emits light. In turn, the light detector may collect light emitted by the phosphor anode in order to image the sample 106. The light detector may include any light detector known in the art, such as, but not limited to, a CCD detector or a CCD-TDI detector.

Figure 2B:
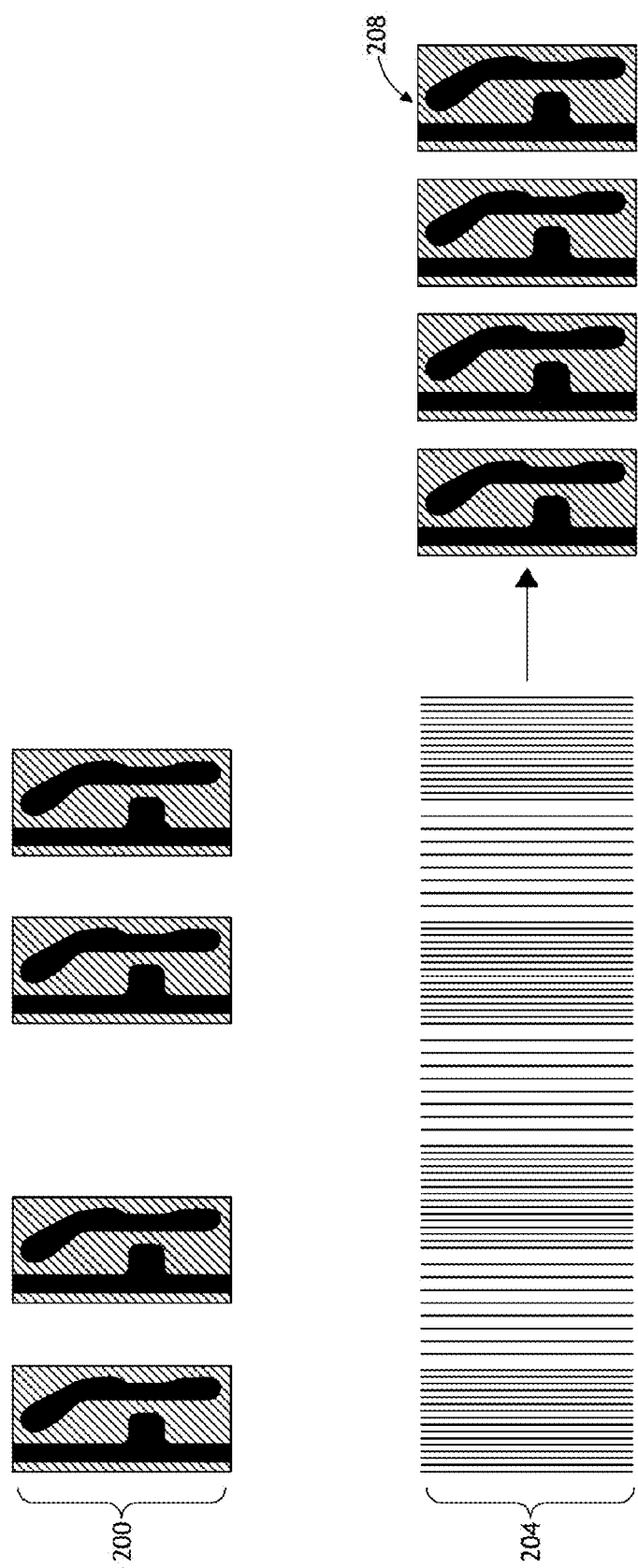

FIGS. 2A-2E illustrate a series of conceptual views of implementations of system 100 and/or method 600, in accordance with the present disclosure. FIGS. 2A and 2B illustrate the varying of scan-line density in accordance with the local pattern complexity of the sample 106, in accordance with one or more embodiments of the present invention. In one embodiment, the system 100 may utilize equally space scan patterns, as shown by 202 and 204. As shown in FIG. 2A, in cases where areas between repeating sample patterns 200 are of no interest, the system 100 may skip these middling areas when scanning. A scanned image of this configuration is depicted in 206. As shown in FIG. 2B, in cases where the areas between the patterns 200 are of interest, but a factor exists allowing for sparser sampling between the patterns 200, the system 100 may apply a modified scanning pattern 204 when scanning these areas. For example, a modified scanning pattern, such as that shown in 204, may be implemented when the defect sizes in these areas are expected to be larger. A scanned image of this configuration is depicted in 208.

Figure 2C:
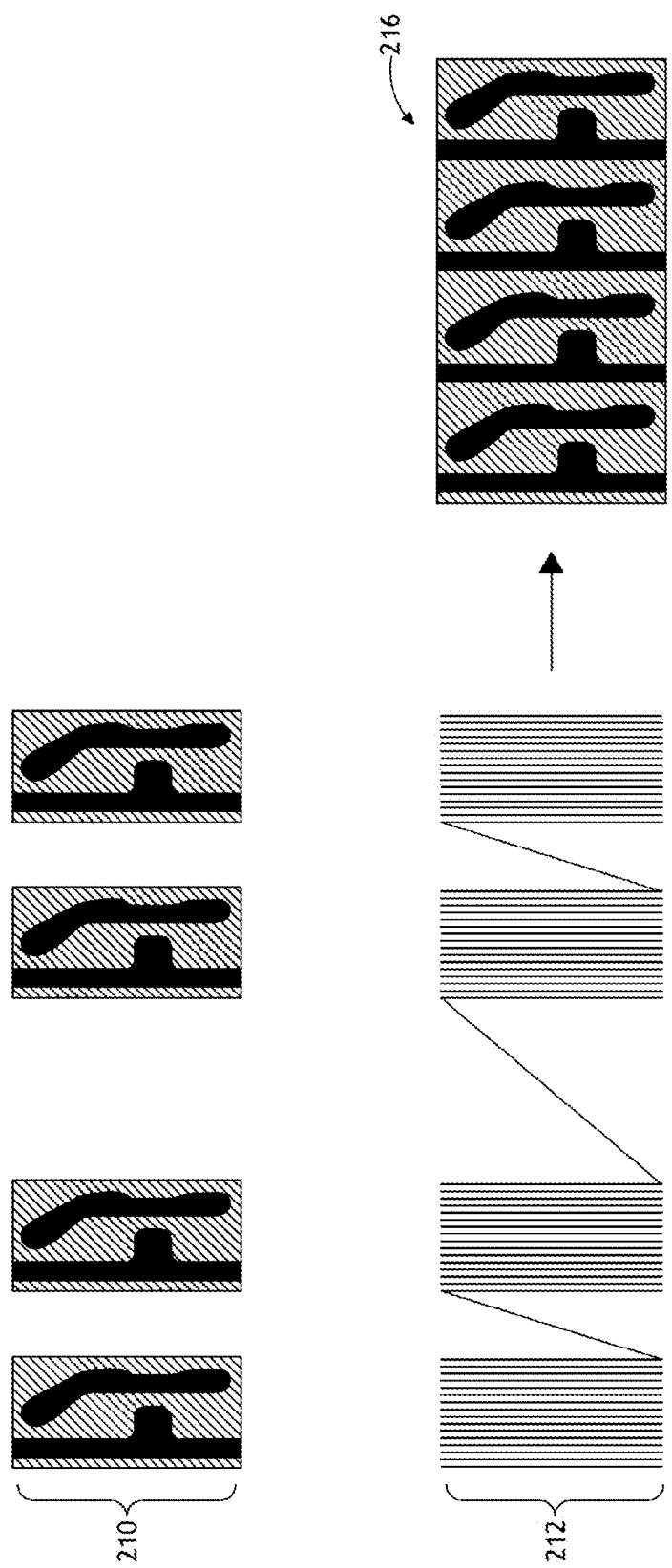
Figure 2D:
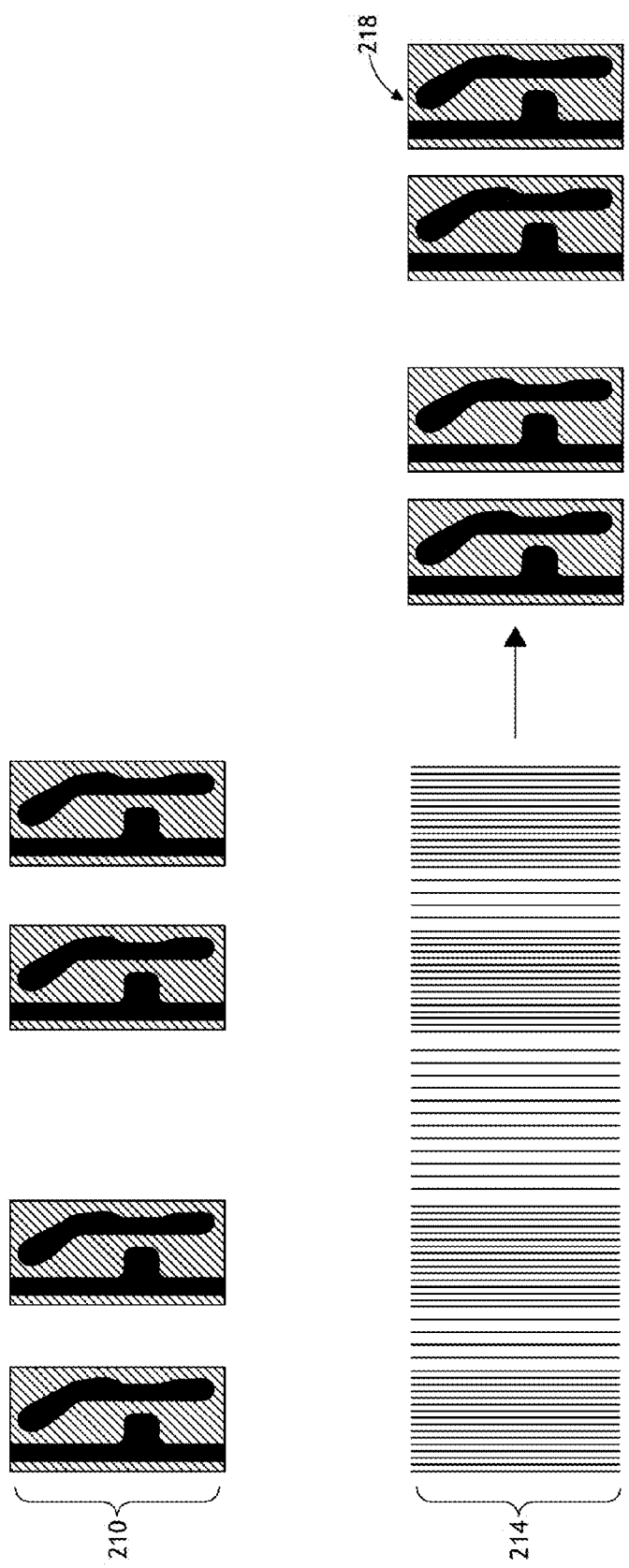

FIGS. 2C and 2D illustrate the varying of scan-line density in accordance with the pattern complexity of the sample 106, in accordance with one or more embodiments of the present invention. In one embodiment, the system 100 may utilize variably-spaced scan patterns, as shown by 212 and 214. As shown in FIG. 2C, in cases where areas between repeating sample patterns 210 are of no interest, the system 100 may skip these middling areas when scanning. A scanned image of this configuration is depicted in 216. As shown in FIG. 2D, in cases where the areas between the patterns 210 are of interest, but a factor exists allowing for sparser sampling between the patterns 210, the system 100 may apply a modified scanning pattern 214 when scanning these areas. For example, a modified scanning pattern, such as that shown in 214, may be implemented when the defect sizes in these areas are expected to be larger. A scanned image of this configuration is depicted in 218.

Figure 2E:
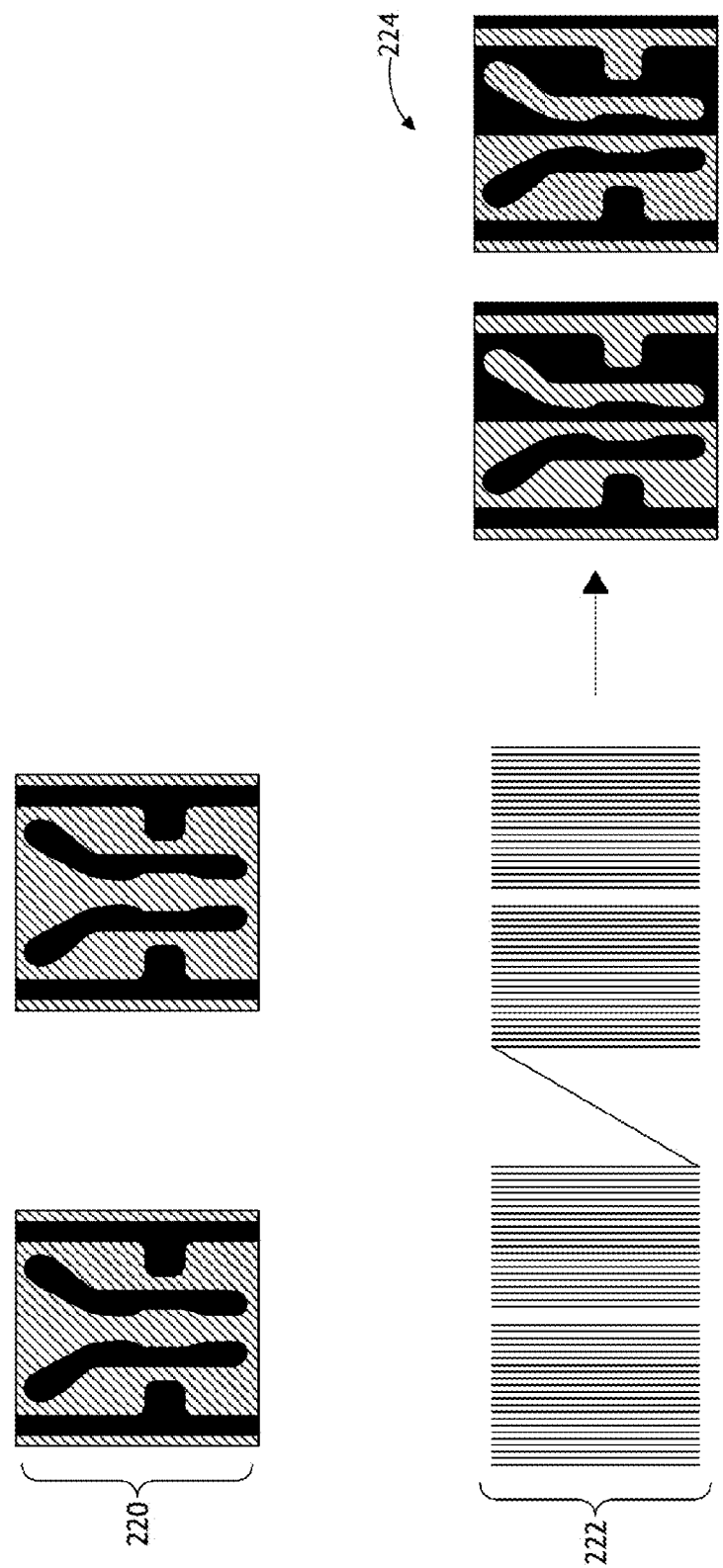

FIG. 2E illustrates the varying of scan pattern and/or imaging parameters implemented by system 100 and/or method 600, in accordance with one or more embodiments of the present invention. In one embodiment, the scan pattern and/or imaging parameters varied by the system 100 may include, but are not limited to, electron landing energy on the sample, extraction field for imaging electrons and the like. In another embodiment, the scan pattern and/or imaging parameters may be varied by the system 100 in order to enhance defect signal levels or otherwise make one or more defects of interest more readily detectable for each sub-area. As a result, different type of defects of interest, which may be region-specific, may be contrast-enhanced and captured during the same inspection. For example, 220 of FIG. 2E depicts a repeating pattern 220, which each may include two or more regions, each region with a different defects type. Scanning pattern 222 may be utilized to scan such a repeating pattern, where the imaging parameters are changed dynamically for the purposes of detecting two or more defect types in different regions in one inspection. Image 224 depicts a result image captured with system 100, which depicts region-specific contrast enhancement.

Figure 3A:
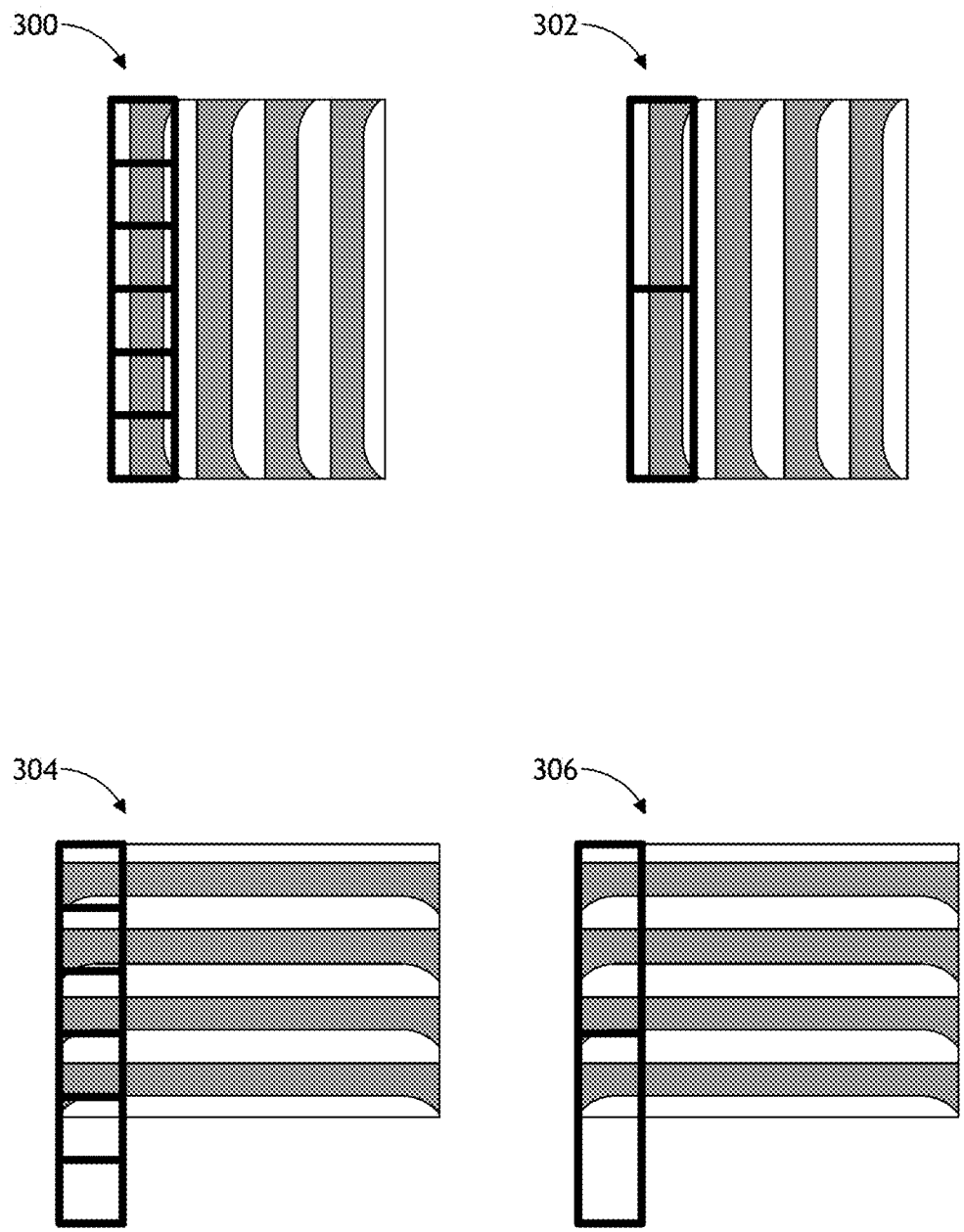
FIGS. 3A-3B are conceptual views of a series of adaptive electron beam scanning scenarios involving the elongation of pixels along a selected direction, in accordance with embodiments of the present invention.
Figure 3B:
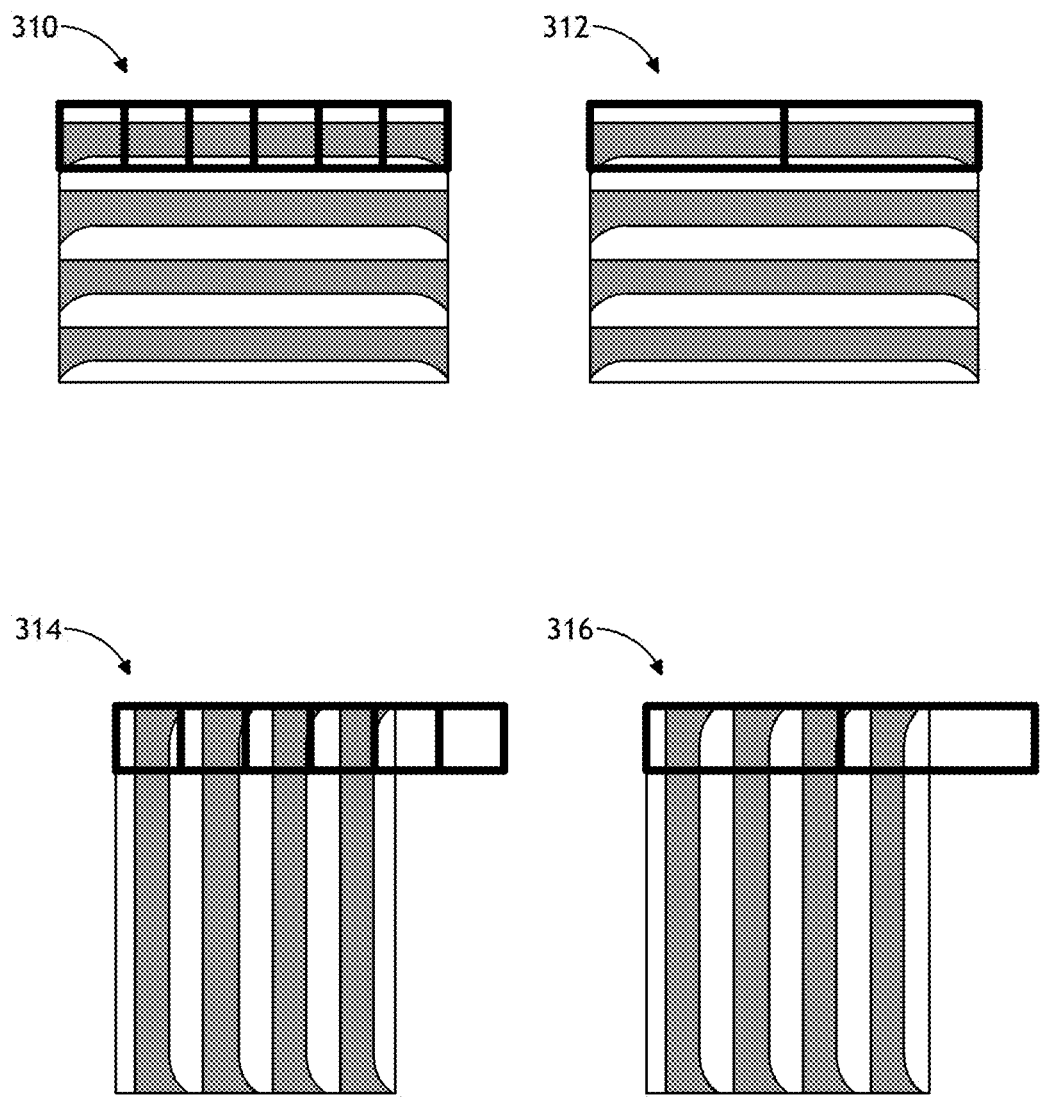

FIGS. 3A-3B illustrate a series of conceptual views of elongation of pixels implemented with system 100 and/or method 600, in accordance with the present disclosure. In one embodiment, the controller 102 may elongate one or more pixels along a selected direction.

In one embodiment, as shown in image 300 and 302 of FIG. 3A, the controller 102 may elongate one or more pixels along an electron beam scan direction by increasing beam scan range by a selected factor E (e.g., E=1-10) and maintaining stage speed and pixel data rate. It is noted that this elongation may lead to rectangular-shaped pixels as depicted in image 302. In another embodiment, the controller 102 may elongate one or more pixels along an electron beam scan direction by increasing scan voltage by a select factor E.

It is noted herein that for certain sample layer geometries, the foregoing approach may significantly speed up inspection without a significant loss of inspection sensitivity. In this regard, an effectively rectangular beam shape may be achieved. It is further noted that in cases where the beam scan direction is along one or more structure lines, as shown in image 302, an improved signal to noise ratio may be achieved as the beam shape matches the pixel shape. In cases where the beam scan direction is perpendicular (or non-parallel in general), as shown in images 304 and 306, a significant under-sampling is achieved.

In another embodiment, as shown in images 310 and 312 of FIG. 3B, the controller 102 may elongate one or more pixels along a direction perpendicular to an electron beam scan direction by increasing stage speed by a selected factor E and maintaining beam scan range and pixel data rate. In this regard, the square pixels of image 310 become rectangular pixels as shown in 312. In cases where the beam scan direction is along one or more structure lines, as shown in images 314 and 316, a significant under-sampling is achieved.

Figure 4A:
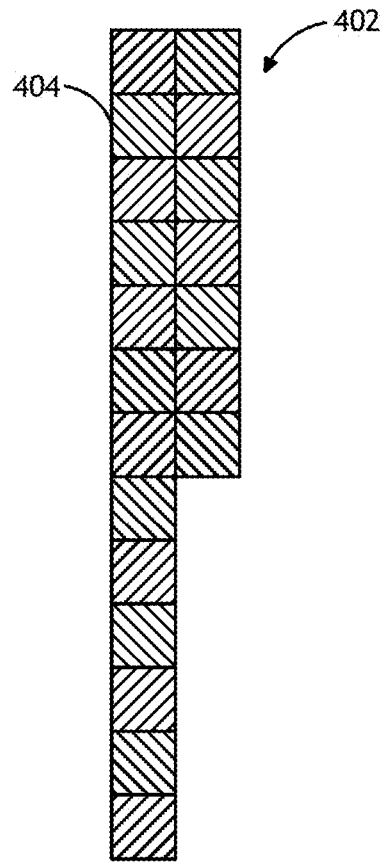
FIGS. 4A-4B are conceptual views of a series of adaptive electron beam scanning scenarios involving the elongation of pixels along a selected direction, in accordance with embodiments of the present invention.
Figure 4B:
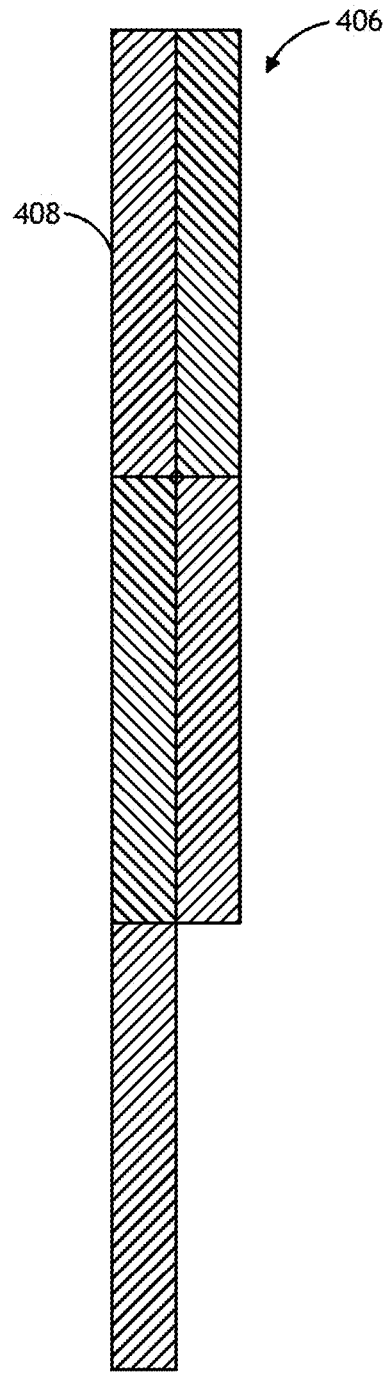

FIGS. 4A-4B illustrate a series of conceptual views of the elongation of pixels utilizing system 100 and/or method 600, in accordance with the present disclosure. It is noted herein that previous scanning methods failed to scan all areas of a sample effectively and risk missing a catastrophic defect. Further, electron beam inspection with adaptive scanning capabilities in the slow scanning direction is not particularly useful for voltage contrast (VC) defect inspection.

In another embodiment, the controller 102 may elongate one or more pixels along the fast electron beam scan direction by increasing scan voltage by a select factor E. It is noted herein that increasing the scanning voltage by a factor E allows the system 100 to increase the deflection of electrons relative to the normal (non-scaled voltage) proportionally to the factor E. In another embodiment, the pixel number of the swath width may be reduced (e.g., 256 pixels wide), allowing the factor E to be increased dramatically (e.g., E>10).

It is noted herein that such a capability provides significant throughput improvement. It is recognized that such an approach is particularly useful in detecting VC defects in straight conductive lines. For example, as shown in image 402 of FIG. 4A, a square non-elongated pixel 404 is depicted. As shown in image 406 of FIG. 4B, an elongated pixel 408 may be created by the controller 102 by increasing scan voltage by a select factor E. In the example depicted in FIG. 4B, the factor corresponds to E=7. In one embodiment, the system 100 may carry out a fast scan along a conductive line, with an elongating factor E, which may charge the conductive line and capture VC variations caused by electrical defects (e.g., broken lines, short between lines and non-opened contact plugs causing an open circuit of the conductive lines to ground). It is noted herein that the above values for the elongating factor E are not limiting and should be interpreted merely as illustrative. For example, the elongating factor may be in the range of 1-10 and further in the range 10-100.

FIGS. 5A-5C illustrate a series of conceptual views of the elongation of pixels utilizing system 100 and/or method 600, in accordance with the present disclosure. FIG. 5A depicts a conceptual view of a SEM image 502 captured with a normal square pixel scan. Image 504 of FIG. 5B depicts a conceptual view of an elongated pixel having E=7. FIG. 5C depicts a conceptual view of a SEM image 502 captured with an elongated pixel with E=7.

In one embodiment, the controller 102 includes one or more processors (not shown) configured to execute program instructions suitable for causing the one or more processors to execute one or more steps described in the present disclosure. In one embodiment, the one or more processors of the controller 102 may be in communication with a carrier medium (e.g., non-transitory storage medium (i.e., memory medium)) containing the program instructions configured to cause the one or more processors of the controller 102 to carry out the various steps described through the present disclosure. It should be recognized that the various steps described throughout the present disclosure may be carried out by a single computing system or, alternatively, a multiple computing system. The controller 102 may include, but is not limited to, a personal computer system, mainframe computer system, workstation, image computer, parallel processor, or any other device known in the art. In general, the term "computer system" may be broadly defined to encompass any device having one or more processors, which execute instructions from a memory medium. Moreover, different subsystems of the system 100 may include a computer system or logic elements suitable for carrying out at least a portion of the steps described above. Therefore, the above description should not be interpreted as a limitation on the present invention but merely an illustration.

The controller 102 may be communicatively coupled to one or more portions of the inspection sub-system 101 via any transmission medium known in the art. For example, the controller 102 may be communicatively coupled to one or more portions of the inspection sub-system 101 via a wireline transmission link or a wireless transmission link. In this manner, the transmission medium may serve as a data link between the controller 102 and other subsystems of the system 100.

The embodiments of the system 100 illustrated in FIG. 1A may be further configured as described herein. In addition, the system 100 may be configured to perform any other step(s) of any of the method embodiment(s) described herein.

Figure 6:
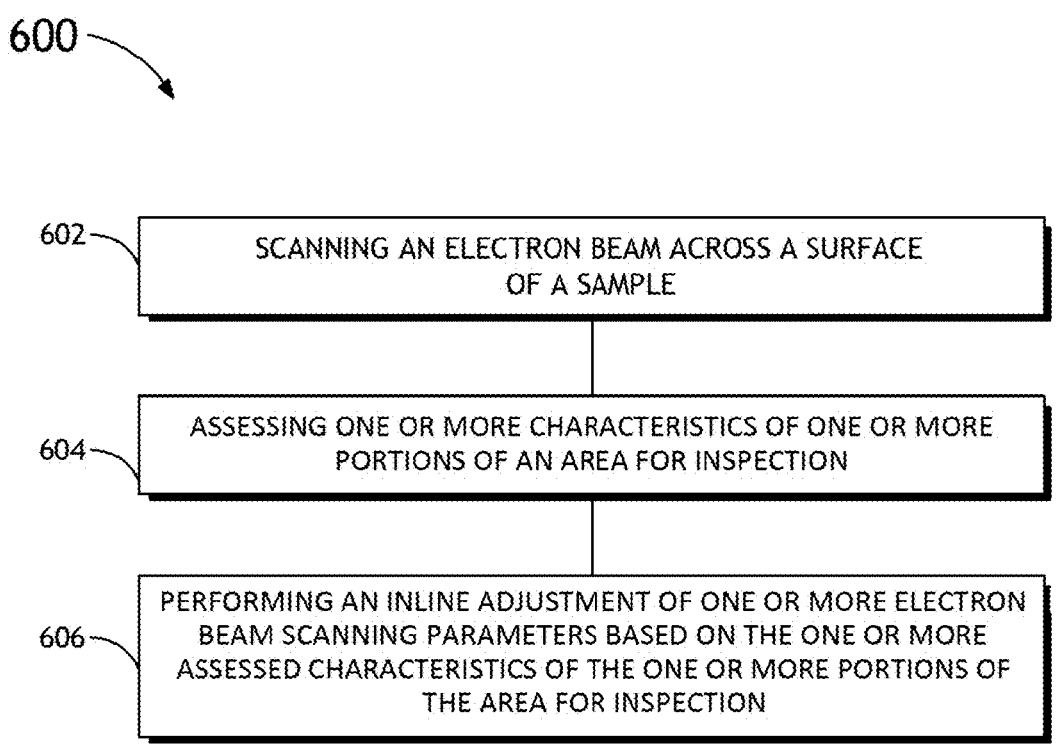
FIG. 6 is a process flow diagram illustrating a method for adaptively scanning a sample during electron beam inspection, in accordance with one embodiment of the present invention.

FIG. 6 is a flow diagram illustrating steps performed in a method for adaptively scanning a sample during electron beam inspection. It is recognized that steps of the process flow 600 may be carried out via pre-programmed instructions executed by one or more processors of controller 102. It should, however, be recognized by those skilled in the art, that the system 100 should not be interpreted as a limitation on process 600 as it is contemplated that a variety of system configurations may carry out process flow 600.

In a first step 602, an electron beam across a surface of the sample. For example, as shown in FIG. 1A, an electron beam 104 may be scanned in accordance with a swath mode inspection procedure or a step-and-scan mode inspection procedure. For instance, one or more scanning elements 111 and/or stage 108 may be utilized to translate the electron beam 104 along a selected pattern across the surface of the sample 106.

In a second step 604, one or more characteristics of one or more portions of an area (or sub-area) for inspection are assessed. For example, the controller 102 may assess (or determine or measure) one or more characteristics of one or more portions of an area (or sub-area) for inspection. For instance, the controller 102 may analyze pattern data acquired by detector assembly 118 associated with the area (or sub-area) for inspection. In another instance, the controller 102 may analyze predicted pattern data based on one or more anticipated device features (e.g., repeating structures and etc.).

In a third step 606, an inline adjustment of one or more scan parameters associated with the scanning of the electron beam across the surface of the sample is performed based on the one or more assessed characteristics of the of one or more portions of the area for inspection. For example, the controller 102 may perform an inline adjustment of one or more scan parameters associated with the scanning of the electron beam across the surface of the sample based on the one or more assessed characteristics of the of one or more portions of the area for inspection.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

It is further contemplated that each of the embodiments of the method described above may include any other step(s) of any other method(s) described herein. In addition, each of the embodiments of the method described above may be performed by any of the systems described herein.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed:

1. A system comprising:
   an inspection sub-system including:
      an electron beam source configured to generate one or more electron beams,
      a sample stage configured to secure the sample;
   a set of electron-optic elements configured to direct the one or more electron beams onto the sample; and
   a detector assembly including at least an electron collector, the detector configured to detect electrons from the surface of the sample; and
   a controller communicatively coupled to one or more portions of the inspection sub-system, the controller including one or more processors configured to execute program instructions configured to cause the one or more processors to adjust one or more parameters of the inspection sub-system, in response to one or more assessed characteristics of one or more portions of an area for inspection.

2. The system of claim 1, wherein the inspection sub-system is configured to inspect a surface of one or more wafers.

3. The system of claim 1, wherein the electron beam source includes one or more electron guns.

4. The system of claim 1, wherein the sample stage comprises:
   at least one of a linear sample stage and a rotational sample stage.

5. The system of claim 1, wherein the one or more parameters of the inspection sub-system adjusted by the controller comprise:
   one or more stage parameters.

6. The system of claim 5, wherein the one or more stage parameters comprise:
   at least one of stage scanning speed or sample bias voltage.

7. The system of claim 1, wherein the one or more parameters of the inspection sub-system adjusted by the controller comprise:
   one or more electron-optic parameters.

8. The system of claim 7, wherein the one or more electron-optics parameters comprise:
   one or more electron-optic focus parameters.

9. The system of claim 1, wherein the one or more parameters of the inspection sub-system adjusted by the controller comprise:
   one or more electron beam scanning parameters.

10. The system of claim 9, wherein the one or more electron beam scanning parameters comprise:
    at least one of scanning pattern, scan-line density, scan-line spacing, electron beam scanning speed, scanning range or field of scanning.

11. The system of claim 1, wherein the one or more parameters of the inspection sub-system adjusted by the controller comprise:
    one or more image forming parameters.

12. The system of claim 11, wherein the one or more image forming parameters comprise:
    at least one of extraction voltage, extraction field strength for secondary electrons or electron landing energy.

13. The system of claim 1, wherein the one or more parameters of the inspection sub-system adjusted by the controller comprise:
    one or more digitization parameters.

14. The system of claim 13, wherein the one or more digitization parameters comprise:
    at least one of digitization rate or pixel data rate.

15. The system of claim 1, wherein the one or more characteristics of one or more portions of an area for inspection comprise:
    a complexity metric of one or more patterns within the one or more portions of the area for inspection.

16. The system of claim 1, wherein the one or more assessed characteristics of one or more portions of an area for inspection comprise:
    a structural characteristic of one or more patterns within the one or more portions of the area for inspection.

17. The system of claim 1, wherein the one or more assessed characteristics of one or more portions of an area for inspection comprise:

a defect density within the one or more portions of the area for inspection.

18. The system of claim 1, wherein the one or more assessed characteristics of one or more portions of an area for inspection comprise:
a defect size within the one or more portions of the area for inspection.

19. The system of claim 1, wherein the one or more assessed characteristics of one or more portions of an area for inspection comprise:
a defect type within the one or more portions of the area for inspection.

20. The system of claim 1, wherein the controller is configured to assess the one or more characteristics of one or more portions of an area for inspection during an inspection recipe setup.

21. The system of claim 1, wherein the controller is configured to assess the one or more characteristics of one or more portions of an area for inspection during a setup inspection run prior to inspection.

22. The system of claim 1, wherein the controller is configured to assess the one or more characteristics of one or more portions of an area for inspection during inspection runtime.

23. The system of claim 1, wherein the controller is communicatively coupled to the electron source and is configured to control one or more electron source parameters.

24. The system of claim 1, wherein the controller is communicatively coupled to the sample stage and is configured to control one or more stage parameters of the sample disposed on the sample stage.

25. The system of claim 1, wherein the controller is communicatively coupled to one or more electron-optic elements of the set of electron-optic elements and is configured to control one or more electron-optic parameters.

26. The system of claim 1, wherein the set of electron-optic elements includes one or more electron optic lenses for focusing the one or more electron beams onto the surface of the sample.

27. The system of claim 26, wherein the controller is communicatively coupled to the one or more electron-optic lenses of the set of electron-optic elements and is configured to control one or more electron-optic focus parameters.

28. The system of claim 1, wherein the set of electron-optic elements includes one or more electron beam scanning elements configured to scan the one or more electron beams across the surface of the sample.

29. The system of claim 28, wherein the controller is communicatively coupled to the one or more electron beam scanning elements and is configured to control one or more electron beam scanning parameters with the electron beam scanning coils.

30. The system of claim 1, wherein the controller is communicatively coupled to a portion of the detector assembly.

31. The system of claim 30, wherein the controller is communicatively coupled to the electron collector of the detector assembly and is configured to control one or more image forming parameters.

32. The system of claim 1, wherein the controller is communicatively coupled to the detector assembly and is configured to control at least one digitization parameter of the detector assembly.

33. The system of claim 1, wherein the detector assembly further includes a scintillating element and a photomultiplier tube.

34. The system of claim 33, wherein the detector assembly further includes a light detector.

35. The system of claim 1, wherein the controller is configured to elongate one or more pixels along a selected direction.

36. A method comprising:
directing one or more electron beams onto a surface of a sample;
assessing one or more characteristics of one or more portions of an area for inspection; and
performing an inline adjustment of one or more parameters associated with the one or more electron beams directed onto the surface of the sample based on the one or more assessed characteristics of the of one or more portions of the area for inspection.

* * * * *